United States Patent [19]

Emery et al.

[11] 4,432,751

[45] Feb. 21, 1984

[54] MONOCLONAL ANTIBODIES AGAINST LENS EPITHELIAL CELLS AND PREVENTING PROLIFERATION OF REMNANT LENS EPITHELIAL CELLS AFTER EXTRACAPSULAR EXTRACTION

[75] Inventors: Jared M. Emery; Dominic M. Lam, both of Houston, Tex.

[73] Assignee: Baylor College of Medicine, Houston, Tex.

[21] Appl. No.: 355,081

[22] Filed: Mar. 5, 1982

[51] Int. Cl.³ .............................................. A61B 19/00
[52] U.S. Cl. ...................................... 604/49; 128/1 R
[58] Field of Search ................. 128/1 R; 604/49, 172; 424/1, 115; 435/68

[56] References Cited

U.S. PATENT DOCUMENTS

| | | | |
|---|---|---|---|
| 4,307,082 | 12/1981 | Rosenberg | 424/115 |
| 4,342,828 | 8/1982 | Takaku et al. | 435/68 |
| 4,349,528 | 9/1982 | Koprowski et al. | 435/68 |

*Primary Examiner*—C. Fred Rosenbaum
*Assistant Examiner*—T. J. Wallen

*Attorney, Agent, or Firm*—Fulbright & Jaworski

[57] ABSTRACT

Disclosed are monoclonal antibodies against lens epithelial cells and methods of producing them. Continuous cell lines for producing monoclonal antibodies to lens epithelial cells are disclosed. Human lens epithelial antibody producing cells are fused with myeloma cells to provide a fused hybrid, the hybrid is cultured, and antibodies specific to human lens epithelial cells are collected.

Proliferation of remnant lens epithelial cells after extracapsular extraction is prevented by instilling the monoclonal antibodies specific to lens epithelial cells into the anterior chamber of the human eye and allowed to interact with the lens epithelial cells. Complement is then instilled into the anterior chamber to cause lysis or other damage to the lens epithelial cells thereby preventing them from multiplying and migrating to cover the surface of the lens capsule left in place. This can be done at the time of extracapsular cataract extraction or later to remove a second cataract caused by proliferation of these cells. There is no damage to other parts of the eye, but only to the remnant lens epithelial cells.

3 Claims, No Drawings

MONOCLONAL ANTIBODIES AGAINST LENS EPITHELIAL CELLS AND PREVENTING PROLIFERATION OF REMNANT LENS EPITHELIAL CELLS AFTER EXTRACAPSULAR EXTRACTION

BACKGROUND OF THE INVENTION

Extracapsular cataract extraction has recently become a more popular method of removing cataracts, probably because of its lower incidence of post-operative complications in terms of cystoid macular edema and possible retinal detachment. The advent of an improved extracapsular extraction technique such as phacoemulsification and the requirement of an intact posterior lens capsule for implantation of a wide variety of intraocular lenses have certainly played an important role in influencing such a trend. The only possible disadvantage of extracapsular cataract extraction is the high incidence of posterior lens capsule opacification, which requires additional surgical procedures (posterior capsulotomy or repolishing of the posterior lens capsule) to obtain good vision.

The pathogenesis of posterior lens capsule opacification after extracapsular cataract extraction is known: the remnant lens epithelial cells proliferate on the posterior lens capsule to form abortive lens "fibers" and "bladder" cells (i.e. Elschnig's pearls).

As reported in Contact and Intraocular Lens Medical Journal, Vol. 5, No. 4, October/December 1979, pp. 175-178, After-Cataract: Studies of Chemical and Radiation Inhibition, by Roy et al, chemical and radiation means have been attempted to try to find a method associated with extracapsular cataract surgery which would lower the incident of after cataract growth. As reported in this publication the chemicals used (vincristine and vinblastine) were tried to chemically inhibit subcapsular epithelial cells because they had been found to have a direct inhibitory effect on cell mitotis (Goodman, L. S., and Gillman, A: The Pharmacological Basis of Therapeutics, Maximilan, New York, 1965, pp. 1373-1376). Vincristine and vinblastine were found to inhibit the corneal wound so that it healed poorly, and because of the deletory effects to the cornea and iris it was the opinion of the authors that these drugs should not be used in further animal studies to try to inhibit subcapsular epithelial proliferation. The authors further stated that radiation given the second day after surgery appeared to be the most effective of all dosage schedules, however, they indicate that there is some danger of injury, the authors concluding that it is difficult to say, however, that if one used radiation in humans whether there would be problems or not.

The authors further pointed out that if there were a drug or chemical system that could be found which would inhibit selectively the subcapsular epithelial cells, this might be a useful way to help prevent after cataracts.

Applicants are aware of the instillation of the mitotic inhibitors methotrexate and retinoic acid, or mixtures thereof, in the anterior chamber of the eye in minimal effective dosages at the end of one lens epithelial cell cycle, which instillation effectively prevents posterior lens capsule opacification without ocular compromise after extracapsular cataract extraction.

Methotrexate is a cycle-dependent anti-metabolite which inhibits the enzyme dihydrofolate reductase and thus interferes with the maintenance of intracellular pool of reduced folates.

Retinoic acid, the exact mechanism being unknown, appears to inhibit either cellular division or DNA synthesis or both.

The present invention constitutes an improvement by producing and the use of monoclonal antibodies specific to residual lens epithelial cells which can be used to destroy these cells selectively without damage to other parts of the eye at the time of the original cataract removal.

PRIOR ART STATEMENT

Applicants are unaware of any art teaching the production of monoclonal antibodies specific to lens epithelial cells or the use of such antibodies to selectively destroy these residual lens epithelial cells without damage to other parts of the eye.

Representative examples of the prior art relating to the production of monoclonal antibodies are as follows: Monoclonal Antibodies, 1980, Plenum Press, New York, edited by Roger H. Kennett, Thomas J. McKearn, and Cathleen B. Bechtol; continuous cultures of fused cells secreting antibody of predefined specificity, Nature, Vol. 256, Aug. 7, 1975, pp. 495-497 and the following U.S. Patents relating to the production of monoclonal antibodies; U.S. Pat. Nos. 4,271,145; 4,196,265; 4,172,124; 4,195,125; 4,262,090; and 4,294,927.

SUMMARY OF THE INVENTION

The present invention is directed to monoclonal antibodies specific to lens epithelial cells, methods of producing them including continuous cell lines from which they are harvested, and the use of them to destroy the residual lens epithelial cells selectively without damage to other parts of the eye at the time of original cataract removal or later for the removal of an after cataract. The monoclonal antibodies are instilled into the anterior chamber of the human eye and allowed to interact with the lens epithelial cells. Complement is then instilled into the anterior chamber to cause selective lysis or other damage to the lens epithelial cells without damage to other parts of the eye. This represents a profound advance over the use of mitotic inhibitors and other methods in that destruction is specific only to the remnant lens epithelial cells which otherwise multiply and migrate to cover the surface of the posterior capsule left in place in the eye which causes a "secondary cataract" resulting in loss of vision requiring a second operation.

Accordingly, it is an object of the present invention to provide monoclonal antibodies specific to lens epithelial cells.

A further object of the present invention is the provision of a continuous cell line for producing monoclonal antibodies specific to lens epithelial cells.

A further object of the present invention is the prevention of opacification of the lens capsule due to residual lens epithelial cells multiplying and migrating to cover its surface after extracapsular cataract extraction by instilling monoclonal antibodies specific to lens epithelial cells at the time of removal of the original cataract, permitting these antibodies to interact with these remnant lens epithelial cells, and then instilling complement which lysis these cells.

A further object of the invention is the removal of after cataracts caused by lens epithelial cell growth and migration by instilling monoclonal antibodies into the anterior chamber of the eye, permitting these antibodies to react with these lens epithelial cells, and then instilling complement which lysis these calls.

Other and further objects, features and advantages of the invention appear throughout.

DESCRIPTION OF THE PREFERRED EMBODIMENTS

The present invention is directed to methods of preventing proliferation of remnant lens epithelial cells after extracapsular extraction by instilling monoclonal antibodies specific to these lens epithelial cells into the anterior chamber of the human eye and allowing them to interact with the lens epithelial cells. Normally, about 100 μl of these monoclonal antibodies is instilled and normally it requires about 30 minutes time for these monoclonal antibodies to interact with the lens epithelial cells. Complement is then instilled into the anterior chamber in an effective amount of about 100 μl which causes lysis or other damage to the residual lens epithelial cells thereby preventing them from multiplying and migrating to cover the surface of the lens capsule left in place. This can be done at the time of extracapsular cataract extraction, preferably immediately after cataract removal, or it can be done later to remove a second cataract caused by proliferation or growth of these cells over the surface of the lens capsule.

These monoclonal antibodies specific to lens epithelial cells are produced by fusing human lens epithelial antibody producing cells with myeloma cells to provide a fused hybrid, the hybrid is cultured, and the antibodies specific to human lens epithelial cells are collected.

The complement is a standard complement, for example, a typical complement and its preparation useful in the present invention is described in Monoclonal Antibodies, supra, at pp. 391-2.

The following are procedures for the production of monoclonal antibodies against lens epithelial cells.

CELL CULTURE

Human lens epithelial cells are obtained either from human eyes within 30 minutes after death, or from tissues removed during cataract surgery. The cells are grown as a monolayer in a tissue culture incubator using well established techniques.

IMMUNIZATION WITH LENS EPITHELIAL CELLS

A mouse (BALB/c or another appropriate strain) is injected intraperitoneally or intravenously with 5-10 million whole cells. Two weeks later a sample of blood from each animal is assayed for a specific antibody. The animal with the highest titer is then injected again intraperitoneally or intravenously with 5-10 million whole cells.

FUSION OF IMMUNE SPLEEN CELLS WITH MYELOMA CELLS

Three to four days after the mouse is immunized (intravenously) the mouse is sacrificed by cervical dislocation. The mouse is bled and the serum is frozen. The mouse is cleaned with 70% ethanol and the spleen is removed aseptically. Using the rubber plunger of a sterile, disposable 3 ml syringe, the spleen is minced through a 50-mesh stainless steel screen with warm HBSS. The suspension is pipeted up and down several times with a 3 ml syringe. A single cell suspension is prepared by passing the suspension through a 200-mesh stainless steel screen. The spleen cells are centrifuged for 10 minutes at 1200 rpm. The red blood cells are analyzed by treatment with 0.83% $NH_4Cl$ for 5 minutes at 40° C. The spleen cells are washed two times in serum-free medium. The cells are counted and their viability determined by the trypan blue dye exclusion test.

The spleen cell suspension is prepared from non-immunized BALB/c mouse for feeder layer on hybrids. The myeloma cells are transferred in exponential growth phase ($5 \times 10^5$ cells/ml) to a 50 ml conical polypropylene centrifuge tube. The myeloma and spleen cell suspension are separately washed two times in serum-free medium. The cells are counted, combined and washed one time to obtain a mixed pellet ($10^8$ spleen cells and $10^7$ myeloma cells). The centrifuge tube is tapped gently to disperse the pellet into a clumpy suspension. 0.8 ml of 50% PEG is added over one minute (37° C.). The suspension is allowed to stand for one minute. One ml serum-free medium is added over another minute. 20 ml serum-free medium is added over 5 minutes.

The cells are centrifuged and resuspended in 60-100 ml of hybridoma medium containing HAT and $2-4 \times 10^7$ spleen cells from normal BALB/c mouse. 0.1 ml aliquots are distributed into 96-well microtest plates and incubated at 37° C. in 10% $CO_2$. An additional 0.1 ml of HT growth medium is added at 7 days when vigorous growth is observed. HY medium is used until sub-cultures are made. Medium change is repeated every 3 to 4 days. When colonies are observed visually (between 12 to 20 days), the clones are screened. 100 ml of culture supernatants are collected for primary screening of antibody activity.

The materials used in the fusion of immune spleen cells with myeloma cells are set forth in the following Table I.

TABLE I

A. Materials:

1. 50% polyethylene glycol (PEG) 1540 (Polysciences)
   1 ml sterile PEG 1540
   1 ml serum-free medium (SF-DMEM)
2. Littlefields' concentration of Thymidine (T) $1.6 \times 10^{-5}M$
   $1.0 \times 10^{-4}M$ - hyposanthine
   $4 \times 10^{-7}M$ - aminopterin
   a. 100 × HT stock solution
      Dissolve: 0.01361 g hypoxanthine
      0.0388 g thymidine in 100 ml of double-distilled water warmed to 70-80° C.
      Filter sterilize, distribute in aliquots and store frozen at −70° C.
   b. 100 × aminopterin stock solution
      Dissolve: 0.018 g in double-distilled water
      Add 0.1 N NaOH dropwise if aminopterin does not dissolve readily. Adjust to pH 7.8.
      Filter sterilize and store frozen at −70° C.
   c. Hybridoma medium
      Dulbecco's MEM with glucose (4.5 g/l)
      L-glutamine added to 4 mM
      2% type 100 rabbit serum
      (Kappa Scientific) 1 mM sodium pyruvate (Gibco)
      100 M MEM non-essential amino acids (Gibco) 50 M
      B-mercaptoethanol 10 mM HEPES
      buffer 5 - ml HAT medium.

ENZYME-LINKED IMMUNOSORBANT ASSAY (ELISA) FOR CELLS

Glutaraldehyde in 0.1 M $NaHCO_3$ is added to each well of a 96-2311 polystyrene microtiter plate 50 µl of 5% and left at room temperature at least 30 minutes. A washed target cells suspension in HEPES-buffered Hank's balanced salt solution (HHBSS) with $10^7$ cells/ml is prepared. The plates are washed three times by filling the wells with distilled water and flicking out the water. They are washed once more with 0.15 M NaCl with 0.01 M $Na_2HPO_4$ (PBS-O), and the liquid flicked out. 50 µl/well of the cell suspension is added and the plates are centrifuged at 1500 RPM for 3 minutes with the brake off. 200 µl/well of 1% formaldehyde in HHBSS is added and left at room temperature for 15 minutes. The plates are centrifuged and the liquid is discarded. The plates are then washed 3 times by pouring PBS-9 into the wells and flicking out the liquid. 50 µl/well of 1% BSA in PBS-9 are added to each plate and left for 10 minutes at room temperature. 50 µl of hybridoma medium samples are added to duplicate wells, SDMEM+2% RS is added to row 1 of each plate and incubated for 90 minutes at room temperature or overnight in the refrigerator. The plates are washed 10 times with 0.05% Triton X-100 in distilled water. 50 µl/well of horseradish peroxidase-conjugated IgG fraction of goat anti-mouse immunoglobulins diluted 1:30 from the frozen stock are added into 0.5 MNaCl, 0.5% Triton X-100, 0.01 M $Na_2HPO_4$, and left for 10 minutes at room temperature. The wells are washed 10 times with 0.05% Triton X-100. 100 µl/well of substrate: 0.1 M sodium citrate containing 1/100 volume 40 mM 2,2'-Azino-di-(3-ethylbenzthiazoline sulfonic acid) diammonium salt (ABTS) and 1/100 30% hydrogen peroxide are added. Substrate is added to row 1 of a blank plate. The titertek spectrophometer is turned on. After 30 minutes the plates are read with the $OD_{414}$. The readings of the medium only (row 1) are averaged for each plate. The means and S.D. are calculated and the samples are considered positive only if mean ±2 S.D. The mean of the controls is subtracted from each positive sample and the specific O.D. is recorded.

CYTOLYSIS OF LENS EPITHELIAL CELLS

The supernatants to be tested are divided in 1- to 5-µl amounts in microwells. The cells are washed in 0.1% BSA and suspended to approximately 2000 cells/µl. 1 µl cells to be tested is added to each well and incubated with the antibodies for ½ hour at room temperature. 5 µl of rabbit serum which gives optimal lysis with control antibody and no lysis when added without additional antibodies are added and incubated at room temperature for 1 hour. The percent of lens epithelial cells killed are read with a microscope.

HISTOLOGICAL CRITERION AND CYTOTOXICITY FOR ANTIBODY SPECIFICITY

Monolayer cultures of lens epithelial cells are treated first with the antibodies and subsequently with complement (as described in the preceding section). The cultures are then observed under the microscope to determine whether all the lens epithelial cells have been lysed. From the previous tests, antibodies from the most promising clones are used to test whether these antibodies indeed destroy only the lens epithelial cells and not other ocular tissues by using intact human eyes or anterior chambers and observing the results histologically. Long-term cytotoxicity and effectiveness of these antibodies are performed by injecting the antibodies and complements into the anterior chambers of monkeys in situ following extracapsular lens extractions. The long-term progress of the treated eyes will be compared with that of the untreated eyes by ophthalmological observations and histological studies.

LARGE SCALE ANTIBODY PRODUCTION

Large scale production of a single monoclonal antibody can be achieved by injecting about $10^7$ hybrid cells into appropriate H-2 compatible mice. Ascites tumors are induced by the following method: For ascites production, mice are injected intraperitoneally with 0.5 ml of pristine (2,6,10,14-tetramethylpentadecane, Aldrich), and rested for 1 to 2 months. 3 to 4 days prior to transfer of the interspecies hybridomas, each mouse is injected with 50 µl of antilymphocyte serum. On the day of tumor transfer, each mouse receives total body irradiation (600 to 800 rads) followed to 6 to 8 hours later by syngenic bone marrow ($10^7$ cells/mouse). Hybridoma cells ($10^6$–$10^7$) in Dulbecco's Modified Eagle's medium are then injected intraperitoneally. As the tumors begin to appear (10 to 30 days after injection), the mice are bled and the presence and concentrations of the antibodies in the serum continually tested. The appropriate antibodies are collected, purified and stored.

Alternate methods for large-scale production of these antibodies include inducing subcutaneous tumors using the method described above. The hydridoma cells grow in tissue culture, and the media which contain the antibodies are continually harvested.

The present invention therefore is well suited and adapted to attain the objects and ends and has the advantages and features mentioned as well as others inherent therein.

While presently preferred embodiments of the invention have been set forth for purposes of disclosure, changes and modifications therein can be made which are within the spirit of the invention as defined by the scope of the appended claims.

What is claimed is:

1. A method of preventing lens epithelial cell growth after extracapsular extraction comprising, instilling into the anterior chamber of an eye after the extracapsular extraction monoclonal antibodies specific to lens epithelial cells, and after a period of time sufficient to permit the monoclonal antibodies to interact with the lens epithelial cells instilling into the anterior chamber a complement effective to cause lysis to the lens epithelial cells.

2. The method of claim 1 wherein, the instilling is immediately after the extracapsular extraction.

3. The method of claim 1 where, the instilling is done after the extracapsular extraction and the lens epithelial cells have migrated at least partially over the lens capsule.

* * * * *